United States Patent [19]

Sellers

[11] Patent Number: 4,915,629
[45] Date of Patent: Apr. 10, 1990

[54] DIRECT ASSEMBLY FRAMEWORK FOR AN OSSEOINTEGRATED IMPLANT

[76] Inventor: Grady C. Sellers, Rte. 3, Box 79, Sulphur Springs, Tex. 75482

[21] Appl. No.: 181,919

[22] Filed: Apr. 15, 1988

[51] Int. Cl.$^4$ ............................................. A61C 8/00
[52] U.S. Cl. .................................................. 433/173
[58] Field of Search ................. 433/173, 174, 175–176

[56] References Cited

U.S. PATENT DOCUMENTS

| 3,499,222 | 3/1970 | Linkow | 433/174 |
|---|---|---|---|
| 3,955,280 | 5/1976 | Sneer | 433/173 |
| 4,086,701 | 5/1978 | Kawahara | 433/174 |
| 4,180,910 | 1/1980 | Straumann | 433/173 |
| 4,324,550 | 4/1982 | Reuther | 433/175 |
| 4,416,629 | 11/1983 | Mozsary | 433/174 |
| 4,431,416 | 2/1984 | Niznick | 433/174 |
| 4,516,937 | 5/1985 | Bosker | 433/173 |
| 4,522,596 | 6/1985 | Ashkinazy | 433/173 |
| 4,552,532 | 11/1985 | Mozsary | 433/173 |
| 4,657,510 | 4/1987 | Gittleman | 433/173 |

FOREIGN PATENT DOCUMENTS

| 2905647 | 2/1979 | Fed. Rep. of Germany . |
| 3413811 | 4/1984 | Fed. Rep. of Germany . |
| 655437 | 4/1985 | United Kingdom . |

OTHER PUBLICATIONS

"Cast Framework Design for Fixed Prosthodontics Supported by Biotes Osseointegrated Implants" by Thomas J. Balshi, DDS, and Nancy Fox, *Trends & Techniques*, Jan./Feb. 1986, vol. 3, No. 1, pp. 30–36.
"Design of Superstructures for Osseointegrated Fixtures" by Iven J. Klineberg and G. M. Murray, *Swedish Dental Journal*, Sep. 28, 1985, pp. 63–69.
"A Fixed Prosthodonic Technique for Mandibular Osseointegrated Titanium Implants" by Larry G. Loos, DDS, MA, *The Journal of Prosthetic Dentistry*, Feb. 1986, vol. 55, No. 2, pp. 232–242.
"The Swedish System of Osseointegrated Implants: Problems and Complications Encountered During a 4-Year Trial Period" by Philip Worthington, Charles L. Bolender, and Thomas D. Taylor, *The International Journal of Oral & Maxillofacial Implants*, vol. 2, No. 2, 1987, pp. 77–84.
"The Longitudinal Clinical Efficacy of Osseointegrated Dental Implants: a 3-Year Report" by J. F. Cox and G. A. Zarb, *The International Journal of Oral & Maxillofacial Implants*, vol. 2, No. 2, 1987, pp. 91–100.
"Modified Single and Short-Span Restorations Supported by Osseointegrated Fixtures in the Partially Edentulous Jaw" by T. Jemt, DDS, PhD, *The Journal of Prosthetic Dentistry*, Feb. 1986, vol. 55, No. 2, pp. 243–246.
"Soldering of Dental Alloys Under Vacuum by IR-Heating" by T. Carlberg and L. Wictorin, *Dental Materials*, Dec. 1986, vol. 2, No. 6, pp. 279–283.
"A Quantitative Study of Preporcelain Soldered Connector Strength with Palladium-Based Porcelain Bonding Alloys" by D. A. Beck, DDS, P. C. Moon, PhD, and C. D. Janus, DDS, MS, *The Journal of Prosthetic Dentistry*, Sep. 1986, vol. 56, No. 3, pp. 301–306.
"Casting Shrinkage in an Ni-Cr FPD" by L. Stevens, *Dental Materials*, Dec. 1987, vol. 3, No. 5, pp. 241–245.

*Primary Examiner*—Robert Peshock
*Attorney, Agent, or Firm*—David H. Judson

[57] ABSTRACT

The present invention relates to a framework adapted to be directly assembly onto an osseointegrated implant. The framework is adapted to be assembled intraorally to allow a precise adaptation of the cast member of the framework to one or more implant-supported abutments. Preferably, the framework includes first and second conical-shaped sleeves adapted to be removably supported in first and second tapered recesses of the cast member. The sleeves cooperate with and are supported by a plurality of cement layers to cushion forces applied to the abutment and to fix the position of the cast member relative to the implant during assembly.

19 Claims, 2 Drawing Sheets

DIRECT ASSEMBLY FRAMEWORK FOR AN OSSEOINTEGRATED IMPLANT

TECHNICAL FIELD

The present invention relates generally to dental restoration and more particularly to a direct assembly framework for use in a tissue-integrated implant system.

BACKGROUND OF THE INVENTION

Many people suffer physically and psychologically from the loss of their teeth. To aid such patients, it is known in the prior art to support a denture on a bone tissue-integrated (i.e., "osseointegrated") implant. Typically, the denture is attached to a cast member which is removably secured to the implant following osseointegration and healing.

Four factors typically affect the success of the prosthesis: patient selection, fixture design and manufacture, surgical technique, and prosthetic technique. Over the last several decades, there has been considerable increase in the success rates associated with tissue-integrated implants due primarily to material advancements and improved surgical techniques. While the current success rates are impressive, there have been few improvements in the techniques used to manufacture and install the prosthesis. This fact is surprising because the prosthetic procedures are crucial to the long-term success of the tissue-integrated implant. Such procedures, however, have not changed fundamentally from techniques used to restore teeth.

To insure a successful result during installation of the prosthesis, the prosthodontist must avoid premature loading, use good bridge design, and work with great accuracy. An ideal implant-supported prosthesis would be a single unit span over all implant abutments, and would reduce the distance opposing forces between abutments could act to approximately one micrometer. Due to the properties of the materials involved, indirect laboratory techniques are not capable of constructing a large cast framework for the prosthesis to this degree of accuracy. When the resulting framework is then fitted on the implant abutments, excessive stress may be present in the system, especially at the points where the coping screws attach the cast framework to the abutments. When excessive forces are then applied to the system, the coping screws may fail or rotate from their seatings. Such imperfect adaptation may allow microscopic flexure to occur, eventual fracture of the framework, or pressure-induced resorption of the bone around the implant.

Prior attempts at reducing stress have involved sectioning the framework into one or more sections and then soldering the sections together. While soldering at one or more points may result in a stable framework, this technique has not overcome the problems of the prior art because stress will not be evenly distributed among the abutments. Moreover, soldering is an indirect procedure subject to inaccuracies, is difficult, and requires an extra appointment for the patient.

There is therefore a need for an improved framework for an osseointegrated implant which overcomes these and other problems associated with prior art techniques.

BRIEF SUMMARY OF THE INVENTION

It is an object of the invention to introduce a novel framework for an osseointegrated implant which can be directly assembled intraorally.

It is yet another object of the present invention to provide a means for fixing the spatial relationship of the framework cast member and the implant abutments during direct assembly of the framework and thereby minimize stress.

It is still another object of the invention to provide a framework which is assembled intraorally which allows a precise adaptation of the framework to the implant-supported abutments.

In the preferred embodiment, the framework includes a one-piece, denture-supporting cast member having an upper surface and a lower surface. The cast member includes a plurality of abutment supports, each adapted to matingly engage an exposed abutment of the osseointegrated implant. Each abutment support is preferably defined by a first tapered recess in the lower surface of the cast member for removably supporting the cast member on an abutment, and a second tapered recess in the upper surface of the cast member. The second tapered recess is located along the same longitudinal axis of the first tapered recess of the abutment support and is adapted to support a coping screw of the framework for securing the cast member to the abutment. The framework also includes a first substantially conical-shaped sleeve supported on each abutment. The outer peripheral surface of the first sleeve is roughened and includes a plurality of substantially horizontal grooves therein for increasing the effective surface area of the sleeve. The direct assembly framework also includes a second substantially conical-shaped sleeve supported in the second tapered recess of each abutment support. The outer peripheral surface of the second sleeve also includes a plurality of substantially horizontal grooves therein for increasing the effective area thereof. The second sleeve is adapted to receive the head of the coping screw which secures the cast member to the abutment. Preferably, one or more cement layers are located within the first and second tapered recesses. These layers cooperate with the first and second sleeves for damping forces which would otherwise cause the framework to move relative to the implant during assembly and in use.

In particular, the sleeves and the cement layers supported in each of the first tapered recesses serve to cushion forces applied to the abutments. Moreover, the sleeves and the cement layers supported in each of the second tapered recesses serve to fix the position of the coping screws relative to the framework upon application of forces to the coping screws. Together, the first and second sleeves cooperate with the cast member to insure that the prosthesis is manufactured and installed much more accurately than is possible with prior art indirect laboratory techniques.

BRIEF DESCRIPTION OF THE DRAWINGS

For a more complete understanding of the present invention and the advantages thereof, reference is now made to the following Description taken in conjunction with the accompanying Drawings in which.

DETAILED DESCRIPTION

Figure 1:
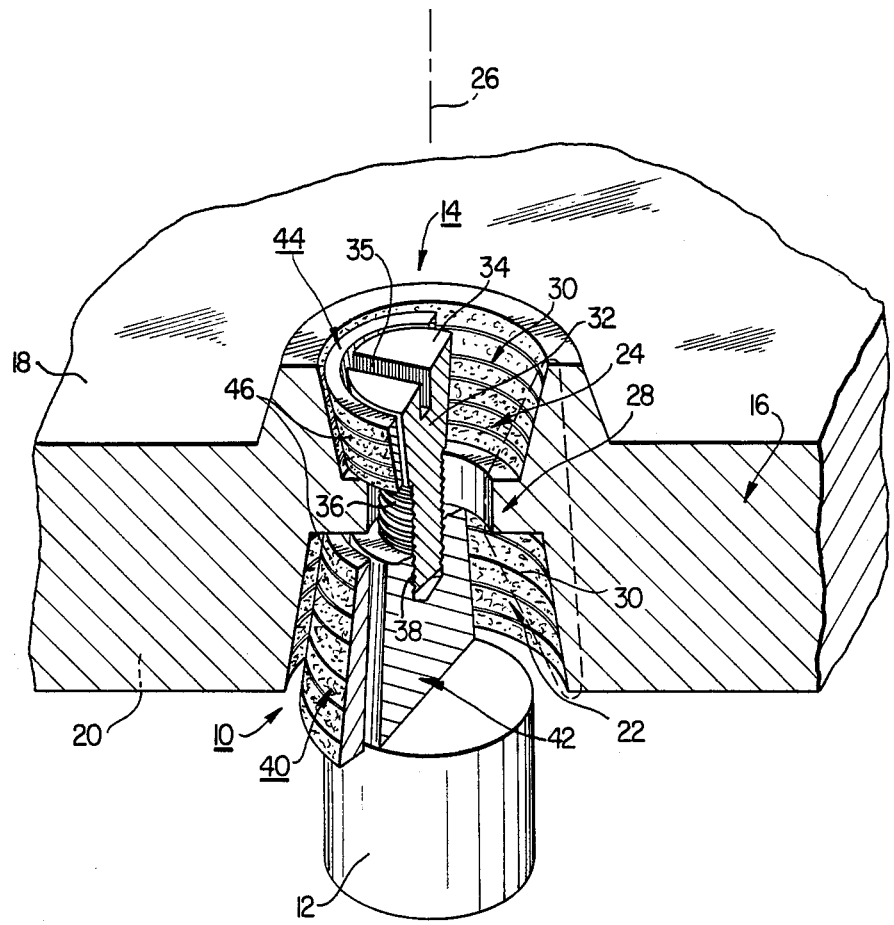
FIG. 1 is a perspective view, partially cutaway, of a portion of a framework of the present invention for use in an osseointegrated implant.

With reference now to the drawings wherein like reference numerals designate like or similar parts throughout the several views, FIG. 1 is a perspective view, partially cutaway, of a portion of a direct assembly framework 10 for use in an osseointegrated implant according to the present invention. Although not shown in detail in FIG. 1, the osseointegrated implant is surgically implanted in the jawbone of the patient and allowed to heal. Thereafter, one or more abutments, such as abutment 12, are secured to the implant in a conventional manner. Each of the abutments 12 is adapted to matingly engage an abutment support 14 of a cast member 16. The cast member 16, which has an upper surface 18 and a lower surface 20, is designed to support one or more false teeth (not shown) for the patient.

The cast member 16 is preferably a one-piece construction made from a silver-free, high content palladium alloy, a dental gold alloy, a titanium alloy, or the like. Each abutment support 14 of the cast member 16 is defined by a first tapered recess 22 in the lower surface 20 of the cast member, and a second tapered recess 24 in the upper surface 18 thereof. While the recesses are shown in FIG. 1 as being tapered, this geometry is not to be taken by way of limitation. As also seen in FIG. 1, the tapered recesses 22 and 24 are in opposed facing relation and are located along the same longitudinal axis 26. The recesses cooperate to form a ledge 28 located at approximately the midpoint of the abutment support. Each of the tapered recesses 22 and 24 also preferably has a rough surface which includes a plurality of small substantially horizontal grooves 30 therein. The grooves 30 effectively increase the surface area of the recesses for the purposes to be described. The cast member 16 is secured to the abutments of the osseointegrated implant via one or more coping screws, such as coping screw 32. Coping screw 32 comprises a substantially conical-shaped head portion 34 having a slot 35, and a threaded portion 36 adapted to engage a threaded portion 38 of the abutment 14.

Figure 2:
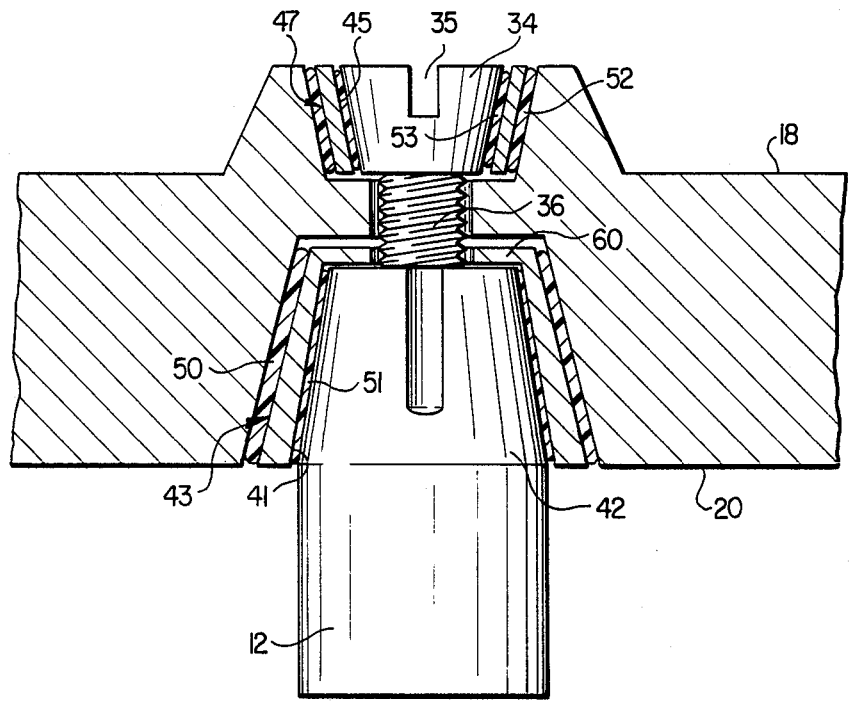
FIG. 2 is a cross-sectional view of an alternate embodiment of the framework wherein each abutment sleeve includes an integral flange.

According to a feature of the invention, the direct assembly framework 10 includes a first sleeve 40 supported on a support post 42 of the abutment 12. Although not meant to be limiting, each "abutment" sleeve 40 preferably has a substantially conical shape to matingly-engage the support post 42. Of course, it should be appreciated that the shape of the sleeve 40 is a function of the shape of the abutment post. As best seen in FIG. 2, sleeve 40 includes an inner peripheral surface 41 and an outer peripheral surface 43. Likewise, the framework 10 includes a second sleeve 44 supported in the second tapered recess 24 between the head portion 34 of the coping screw 32 and the recess. The "coping screw" sleeve 44 also has a substantially conical shape due to the shape of the screw head portion 34, although other sleeve geometries are well within the scope of the invention. Sleeve 44 includes an inner peripheral surface 45 and an outer peripheral surface 47. The outer peripheral surfaces of the sleeves 40 and 44 are coarse and include a plurality of substantially small horizontal grooves 46 for increasing the surface area thereof. The sleeves 40 and 44 are preferably formed of dental gold, titanium or a palladium alloy.

According to a feature of the present invention, a plurality of cement layers are provided in the first and second tapered recesses 22 and 24. These layers cooperate with and are supported by the sleeves 40 and 44 to overcome the problems associated with prior art prosthetic techniques. In the preferred embodiment, each of the cement layers is formed of a self-cure crown cement composition having a polymer and an inorganic filler. One such cement composition is available from Den Mat Corporation of Santa Maria, California. Other types of high compression-strength cements are within the scope of the present invention. As best seen in FIG. 2, a first layer 50 of the cement composition is preferably provided between the outer peripheral surface 43 of the sleeve 40 and the first tapered recess 22. A second layer 52 is preferably located between the outer peripheral surface 47 of the sleeve 44 and the second tapered recess 24. Although not required, a third cement layer 51 may be located between the inner peripheral surface 41 of the sleeve 40 and the support post 42 of the abutment 12. Likewise, a fourth layer 53 may be located between the inner peripheral surface 45 of the sleeve 44 and the head 34 of the coping screw 32. The cement composition is designed to have a compression strength sufficiently high enough to tolerate occlusal forces and a modulus of elasticity sufficiently low enough to help absorb shocks before such forces are transmitted to the jawbone.

The cement layers are thus used to stabilize the relationship of the framework to the support points of the cast member. In this manner, the sleeves and the one or more cement layers advantageously serve to cushion forces applied to the cast member during installation and use. It should also be appreciated that the beneficial damping provided by the cement composition layers is also facilitated in part by the grooves 30 (in the recesses) and the grooves 46 (on the sleeves) which together increase the effective bonding area of the cement.

Therefore, the sleeve 40 and the cement layers 50 and 51 serve to cushion forces applied to each abutment 12. Likewise, the sleeve 44 and the cement layers 52 and 53 serve to attenuate relative movement between the coping screw 32 and the cast member 16 upon application of force to the coping screw. Together, the sleeves and the cement layers cooperate with the cast member 16 to reduce stress normally associated with a prior art osseointegrated prosthesis. Of course, although not shown in detail, it should be appreciated that each of the abutment supports of the cast member have the structure shown in FIGS. 1 and 2.

In the preferred embodiment, the crown cement composition has a compressive strength on the order of $4.1 \times 10^4$ lbs./in$^2$, a tensile strength on the order of $6.3 \times 10^3$ lbs./in$^2$ and a Young's modulus of elasticity of approximately $1.0 \times 10^6$ lbs./in$^2$. Moreover, upon final assembly of the framework, the cement layers 50–53 should be as small as possible (e.g., 0.1 millimeters) to minimize the effects of cure shrinkage (approximately 0.5%).

The various components of the direct assembly framework are custom made for the patient in accordance with the following general steps. The various abutment and coping screw sleeves may be formed from plastic telescopic copings which are normally incorporated into the waxup for the cast member. In particular, the copings are lengthened with sticky wax, cast into Type III dental gold, sectioned and then reshaped to form the sleeves 40 and 44. The sleeves are approximately 0.2 to 0.5 millimeters thick. To form the rough outer peripheral surface of each sleeve, the surface is rubbed with a coarse diamond grit. Thereafter, the small horizontal grooves are formed.

After a sufficient post-operative period, and following verification of the osseointegration with radiograph and percussion, the abutments are screwed onto the implant body. To make the first master impression of the cast member 16, a transfer coping is placed on each abutment 12 and "lifted" with the impression. The impression material used is preferably a polyether sold under the trademark IMPREGUM TM by Premier Dental Products Co. of Norristown, Pennsylvania. Aluminum transfer pins are then positioned and the impression poured with improved dental stone. A facebow transfer is then used to mount the maxillary model on a semi-adjustable articulator. Thereafter, an opposing model is mounted using a wax occlusion rim of the patient's vertical dimension in centered relation.

The sleeves 40 for the abutments are then positioned on the master model. New castable copings are fabricated from an acrylic paste to be incorporated into the waxup. Preferably, the paste is of the type marketed under the trademark DURALAY TM by Reliance Dental Mfg. Co. of Worth, Illinois. A 0.1 mm thick disc of cured DURALAY TM paste is then placed over the sleeves so that a hole just large enough for a coping screw is positioned appropriately. Each coping screw 32 with its sleeve 44 in place is then positioned and screwed to the final desired position. An appropriate lubricant is then applied to the surface of the sleeves to facilitate removal of the sleeves from the castable coping. DURALAY TM paste is then added around the sleeves and the disc. After curing, the coping screws and sleeves are removed from the castable coping. Blue inlay wax is then used to add bulk to the coping as needed. The coping screws, abutment sleeves, coping screw sleeves, and castable copings are then assembled on the master cast and the cast member 16 of the direct assembly framework is then fabricated.

After the direct assembly framework 10 is fabricated, the following steps can be used to assemble the framework intraorally. When assembled, the framework will be accurate to the extent of overall cure shrinkage of the cement in the cement layers. Any abutment which does not have a common path of insertion with the other abutments must be altered in the same manner as a crown preparation until a common path of insertion exists.

The abutment sleeves are placed on their respective abutments so that marked labial or buccal sides are correct. The cast member is tried over the sleeves and relieved as needed until it is fully seated without binding against the sleeves. The coping screws and the coping screw sleeves are then placed one at a time. The cast member is relieved as needed until all of the coping screws are fully seated with the sleeves in place. Once the cast member, coping screw sleeves, abutment sleeves, and coping screws are in their proper intraoral position, these components are removed from the mouth and prepared for cementation.

A coarse diamond is first used to roughen the surface of the cast member so that the cement will contact with the small, horizontal grooves placed for tension. The cast member and sleeves are then cleaned, rinsed, dried, and arranged in sequential order for assembly. Each sleeve is specific for its location in the framework.

The dentist repositions the abutment sleeves intraorally and makes a final check of the correct sleeve position and seating. A bonding agent is applied around the sleeves and inside the first tapered recess of the cast member. Thereafter, cement paste is applied simultaneously around the abutment sleeves and inside the first tapered recesses of the cast member. This cement forms layer 50 as described above. The retentive grooves 30 and 46 should be filled and enough cement present to fill the cement space without great excess. All abutment sleeves are then cemented simultaneously to avoid possible inaccuracies and multiple seatings. The cast member is seated and held with finger pressure until the cement is completely set. The cast member is then taken from the mouth and excess cement thoroughly removed. A bonding agent is then applied to the second tapered recesses of the cast member.

Thereafter, the cast member 16 is repositioned intraorally to verify complete seating and the absolute absence of rocking motion. If rocking movement is detected, the dentist should check for cement or other debris between the cast member and the abutments. Each coping sleeve 44 is thereafter cemented singularly with its own cement mix to form layer 52. A small amount of cement paste can be mixed and then applied to a single coping screw sleeve until it is placed in a casting. Again, the grooves 30 and 46 should be filled in with enough cement to fill the cement space without great excess. After the sleeve 44 is positioned, the coping screw 32 is placed and then rotated until it is completely but very gently seated. Excess cement is then removed before the cement sets. After all the coping screw sleeves 44 are cemented, the coping screws 32 are removed and cleaned of excess cement. The heads 34 of the coping screws may be shortened and the height of the cast member reduced as needed. The framework assembly is now complete. The framework should fit the prosthetic abutments with an accuracy on the order of $10^{-4}$ mm. A well-made one-piece cast member will have a marginal gap of approximately 10 micrometers.

Referring back now to FIG. 2, a cross-sectional view is shown of an alternate embodiment of the direct assembly framework of FIG. 1. In the alternate embodiment of FIG. 2, each of the abutment sleeves 40 includes an integral flange 60 located at an upper end thereof to facilitate the proper seating of the cast member 16 on the associated abutment.

Figure 3:
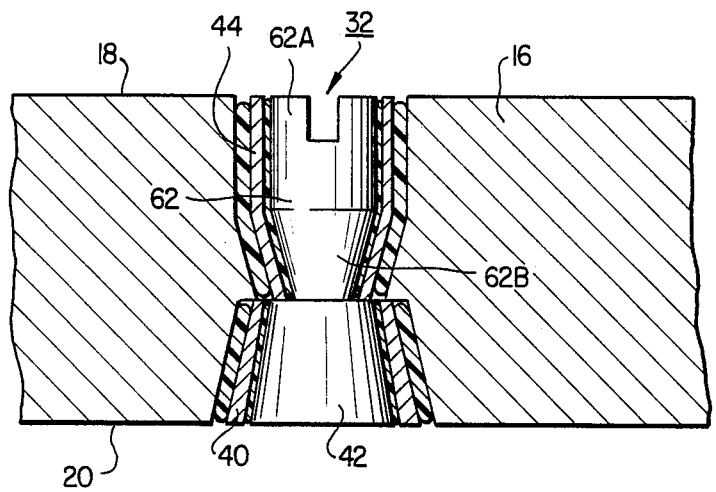
FIG. 3 is a cross-sectional view of another embodiment of the framework for use with a modified-type of coping screw.

As noted above, the geometry of each of the coping screw sleeves is also a direct function of the geometry of the coping screw itself. In particular, and with reference to FIG. 3, a cross-sectional view is shown of yet another embodiment of the direct assembly framework wherein the coping screw 32 includes a head 62 having an upper portion 62A and a lower portion 62B substantially as shown in FIG. 3. When this type of geometry is used for the coping screw, the coping screw sleeve 44 is required to have substantially the shape shown in FIG. 3.

In summary, according to the invention a direct assembly framework is provided comprising a cast member, one or more abutment sleeves, one or more coping sleeves, one or more coping screws and one or more cement layers for securing these components against relative movement. The sleeves are preferably made of dental gold or titanium, and the cement is a self-cured composite resin. The direct assembly of the framework is accomplished intraorally. The prosthesis is constructed and installed in a way which is much more accurate than is possible with prior art indirect laboratory techniques. Soldering and other prior art approaches required to compensate for inaccuracies and defects are therefore not needed. The resulting bone-fixture-prosthesis system is free of internal stress for any number of implants in any length of prosthesis. Moreover, the direct assembly framework advantageously reduces the distance opposing forces act on abutments to a range of 0.5 to 2.5 micrometers.

Although the invention has been described and illustrated in detail, it should appreciated that the same is by way of illustration only, and is not to be taken by way of limitation. The spirit and scope of the present invention are limited only to the terms of the appended claims.

I claim:

1. A framework for a fixed/detachable prosthesis that is assembled intraorally onto at least one abutment supported by an osseointegrated implant, the framework comprising:
   a cast member having an upper surface and a lower surface each including a recess therein, the upper surface for supporting an aesthetic veneer;
   a sleeve supported on the abutment between the abutment and the recess in the lower surface;
   a sleeve supported in the recess in the upper surface;
   fastening means supported in the sleeve in the upper surface for securing the cast member to the abutment; and
   cement means located in the recesses in the upper and lower surfaces to provide accurate adaptation of the cast member to the abutment upon installation of the cast member.

2. The framework as described in claim 1 wherein the cement means is a cement composition having a compression strength sufficiently high enough to tolerate occlusal forces on the implant and having a modulus of elasticity sufficiently low enough to absorb shocks.

3. The framework as described in claim 2 wherein cement means includes a first layer located adjacent an outer peripheral surface of the sleeve supported on the abutment, and a second layer located adjacent the outer peripheral surface of the sleeve supported in the recess in the upper surface.

4. The framework as described in claim 3 wherein the outer peripheral surface of each of the sleeves is coarse and includes a plurality of grooves for increasing the area of said outer peripheral surface.

5. The framework as described in claim 4 wherein the grooves are substantially horizontal.

6. The framework as described in claim 4 wherein each of the recesses is coarse and includes a plurality of grooves for increasing the surface area thereof.

7. The framework as described in claim 6 wherein each of the grooves is substantially horizontal.

8. The framework as described in claim 3 wherein the cement means includes a third layer located adjacent the inner peripheral surface of the sleeve supported on the abutment, and a fourth layer located adjacent the inner peripheral surface of the sleeve supported in the recess in the upper surface.

9. The framework as described in claim 8 wherein each of the layers is a cement composition comprising a polymer and inorganic filler.

10. The framework as described in claim 1 wherein the recesses are located in opposed facing relation along a longitudinal axis of the cast member.

11. The framework as described in claim 1 wherein the sleeve includes an integral flange along a top surface thereof.

12. A framework for a fixed detachable prosthesis that is assembled intraorally onto abutments supported by osseointegrated implants, the framework comprising:
   a one-piece cast member having an upper surface and a lower surface each including a plurality of recesses therein, the upper surface for supporting an aesthetic veneer;
   a substantially conical-shaped sleeve supported on each abutment;
   a substantially conical-shaped sleeve supported in each recess in the upper surface;
   fastening means for securing the cast member to the abutments, the fastening means including a plurality of coping screws each supported in a recess in the upper surface; and
   cement means located in the recess in the upper and lower surfaces to provide accurate adaptation of the cast member to the abutments upon installation of the cast member.

13. The framework as described in claim 12 wherein the tapered recesses are located in opposed facing relation along a longitudinal axis of the cast member.

14. The framework as described in claim 12 wherein the cement means is a self-cure composition comprising a polymer and an inorganic filler.

15. The framework as described in claim 12 wherein the sleeves are formed of dental gold.

16. The framework as described in claim 12 wherein the sleeves are formed of titanium.

17. The framework as described in claim 12 wherein the outer peripheral surfaces of the sleeves include a plurality of substantially horizontal grooves for increasing the area of the sleeves.

18. The framework as described in claim 12 wherein the cast member is formed of a palladium alloy.

19. A method for accurately adapting a cast member on an osseointegrated implant having at least one abutment, the cast member for supporting an aesthetic veneer, comprising the steps of:
   supporting a sleeve on the abutment;
   intraorally cementing the cast member to the sleeve; and
   fastening the cast member to the abutment using a fastener.

* * * * *